(12) United States Patent
Yang et al.

(10) Patent No.: US 11,993,561 B2
(45) Date of Patent: May 28, 2024

(54) EXPECTORANT COMPOUND, PREPARATION METHOD THEREOF AND USE THEREOF

(71) Applicant: HC SYNTHETIC PHARMACEUTICAL CO., LTD., Xi'an (CN)

(72) Inventors: Cheng Yang, Xi'an (CN); Sumin Qi, Xi'an (CN); Qiyuan Zhang, Xi'an (CN); Dongxing Li, Xi'an (CN); Tieshan Chen, Xi'an (CN); Xiaodan Zhao, Xi'an (CN)

(73) Assignee: HC SYNTHETIC PHARMACEUTICAL CO., LTD., Shaanxi Province (CN)

( * ) Notice: Subject to any disclaimer, the term of this patent is extended or adjusted under 35 U.S.C. 154(b) by 275 days.

(21) Appl. No.: 17/769,774

(22) PCT Filed: Jul. 1, 2020

(86) PCT No.: PCT/CN2020/099664
§ 371 (c)(1),
(2) Date: Apr. 18, 2022

(87) PCT Pub. No.: WO2021/082501
PCT Pub. Date: May 6, 2021

(65) Prior Publication Data
US 2022/0388952 A1    Dec. 8, 2022

(30) Foreign Application Priority Data
Oct. 31, 2019   (CN) .......................... 201911055630.8

(51) Int. Cl.
C07C 323/30    (2006.01)
A61K 31/137    (2006.01)
A61P 11/10     (2006.01)

(52) U.S. Cl.
CPC .......... *C07C 323/30* (2013.01); *A61K 31/137* (2013.01); *A61P 11/10* (2018.01)

(58) Field of Classification Search
CPC ............. A61K 31/137; A61P 11/10–14; C07C 323/30
See application file for complete search history.

(56) References Cited

U.S. PATENT DOCUMENTS

2005/0027012 A1* 2/2005 Kohlrausch .......... A61K 9/2054
424/464

FOREIGN PATENT DOCUMENTS

| CN | 1699337   | A | 11/2005 |
|----|-----------|---|---------|
| CN | 101544572 | A | 9/2009  |
| CN | 101756949 | A | 6/2010  |
| CN | 102050748 | A | 5/2011  |
| CN | 105693764 | A | 6/2016  |

OTHER PUBLICATIONS

ISR for PCT/CN2020/099664, Sep. 28, 2020.
Registry RN(103020-54-8,85695-50-7) STN Columbus, Jul. 4, 1986, pp. 1-3.
Kochetkov M.A., et al, "Studies of reactions of dimethylphosphoramidic difluoride with trans-2-(N,N-dialkylamino) cycloalkanols in the presence of various sulfur-containing nucleophiles", Russian Chemical Bulletin, vol. 47, No. 9, Sep. 1998, 1755-1762, Plenum Publishing Corporation.
Medicinal Chemistry, Jul. 1, 1995, p. 97-99.
Champseix, A., et.al., "Syntheses de b-sultames(thiazetidines-1,2 dioxyde-1,1)", Bulletin de la societe Chimique de France 1985 No. 3, p. 463-472.
Barkworth M. R., et.al., "Compounds with Bridgehead Nitrogen, part 43. The Reaction between trans-2-Aminocycloalkanethiols and Formaldehyde", J. Chem. Soc. Perkin Trans. I 1982, p. 2777-2781.
Database Registry ACS [Online], Retrieved from STN Nov. 10, 2013, RN1470521-53-9.

* cited by examiner

*Primary Examiner* — Theodore R. Howell
(74) *Attorney, Agent, or Firm* — AKC PATENTS, LLC; Aliki K. Collins

(57) ABSTRACT

The present disclosure discloses an expectorant compound, and specifically discloses compounds represented by formula I and formula II, pharmaceutically acceptable salts or tautomers thereof.

18 Claims, No Drawings

EXPECTORANT COMPOUND, PREPARATION METHOD THEREOF AND USE THEREOF

CROSS REFERENCE TO RELATED APPLICATION

This disclosure claims the priority of Chinese patent application No. CN201911055630.8 entitled Expectorant Compound, Preparation Method Thereof and Use Thereof filed with China National Intellectual Property Administration on Oct. 31, 2019, which is incorporated herein by reference in its entirety.

TECHNICAL FIELD

The present disclosure relates to an expectorant medicament and its preparation method, namely the compound of formula I and II or their pharmaceutically acceptable salt and the use of the use of the pharmaceutical composition in expectoration;

BACKGROUND

Expectoration is a common symptom of respiratory diseases. The increase of sputum can stimulate the respiratory mucosa and cause cough. Blocking of the bronchioles can not only cause asthma, but also cause secondary infection, further damages the respiratory tract, and aggravates cough, expectoration and asthma. In severe cases, breathing may be suppressed or suffocation may be resulted. Excessive secretion of mucus can cause dysfunction of mucociliary clearance and damage to local defense function, resulting in uncontrollable infection and in aggravation of airway obstruction, which directly affects the progression of the disease and the subjective feelings of patients. Therefore, the use of expectorants to promote the efflux of airway secretions as soon as possible is an important auxiliary measure for the treatment of airway inflammation.

Expectorants are a class of drugs that can thin sputum, reduce its viscosity to facilitate expectoration of sputum or can accelerate the movement of mucociliary in the respiratory tract and improve the function of sputum transport. Expectorants promote the discharge of build-up phlegm in the lumen of the respiratory tract, reduce the irritation to the respiratory mucosa, play the role of antitussive and asthma indirectly, and also help control secondary infections. Expectorant drugs play the role of promoting phlegm efflux in the following aspects: (1) improve the physical and chemical properties of sputum and reduce viscosity. (2) restore the normal structure of airway epithelial mucus layer and the function of ciliary clearance. (3) inhibit the production and secretion of mucin, and reduce the production of high-viscosity mucus. (4) promote DNA depolymerization in purulent sputum. (5) resist inflammation and reduce DNA production. Based on the main effect of the drug, expectorants are divided into mucus secretion promoting drugs (nausea expectorants and irritating expectorants) and mucolytics. Currently, clinically representative chemical expectorants include ammonium chloride, acetylcysteine, ambroxol, erdosteine, etc. However, the above commonly used drugs all have certain adverse reactions, thus it is necessary to develop a new expectorant that is safe and effective.

SUMMARY

The present disclosure relates to compounds represented by formula I and formula II and their non-toxic pharmaceutically acceptable salts, as well as pharmaceutical compositions containing these compounds as active ingredient, and the use of the compounds and pharmaceutical compositions in expectorants. In the present disclosure, by introducing the sulfhydryl group in acetylcystine of the compound into ambroxol or similar structure, the inventors surprisingly found that the therapeutic effect of expectorant is significantly better than that of the existing expectorant. The compounds of the present disclosure have higher safety and improved therapeutic effect.

The first aspect of the present disclosure therefore provides compounds represented by formula I and formula II, and pharmaceutically acceptable salts thereof:

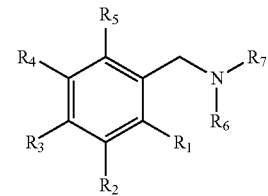

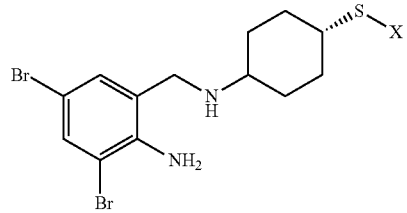

wherein in the compound represented by formula I:
$R_1$ represents H, F, Cl, Br or $NH_2$; $R_2$ represents H, F, Cl or Br; $R_3$ represents H, F, Cl, Br or $NH_2$; $R_4$ represents H, F, Cl or Br; $R_5$ represents H, F, Cl or Br; $R_6$ represents H or $CH_3$; $R_7$ represents

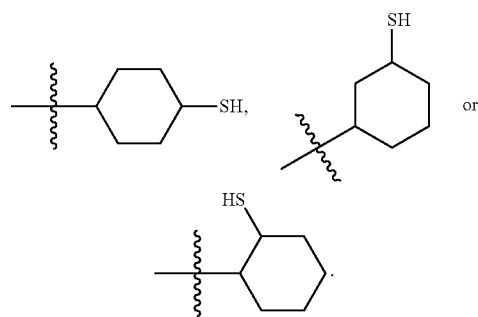

and wherein in the compound represented by formula II:
X represents

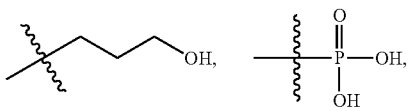 [SMILES: *CCCO ; *P(=O)(O)O]

and their alkali metal salts, salts of amino acid (such as L-alanine, L-valine, etc.).

Preferably, the present disclosure provides compounds represented by formula I and formula II, or pharmaceutically acceptable salts thereof, and the compound is selected from the compounds represented by the following formulas:

I1: trans-4-[(2-amino-3,5-dibromo-benzyl)amino]-cyclohexanethiol
I2: trans-3-[(2-amino-3,5-dibromo-benzyl)amino]-cyclohexanethiol
I3: cis-3-[(2-amino-3,5-dibromo-benzyl)amino]-cyclohexanethiol
I4: trans-4-[(2-amino-3,5-dibromo-benzyl)-methylamino]-cyclohexanethiol
I5: trans-4-[(2-amino-3,5-dibromo-benzyl)-methylamino]-cyclohexanethiol
I6: cis-3-[(2-amino-3,5-dibromo-benzyl)-methylamino]-cyclohexanethiol
I7: trans-2-[(2-amino-3,5-dibromo-benzyl)-methylamino]-cyclohexanethiol
I8: cis-4-[(2-amino-3,5-dibromo-benzyl)-methylamino]-cyclohexanethiol
I9: cis-3-[(4-amino-2-chloro-benzyl)amino]-cyclohexanethiol
I10: cis-3-[(2-amino-5-bromo-benzyl)amino]-cyclohexanethiol
I11: cis-3-[(2-amino-4-chloro-benzyl)amino]-cyclohexanethiol
I12: trans-4-[(2-amino-6-chloro-benzyl)-methylamino]-cyclohexanethiol
I13: trans-3-[4-(2-amino-3,5-dibromo-benzylamino)-cyclohexylsulfanyl]-propane-1-ol Further, the present disclosure provides a method for preparing the compounds represented by the formula I and formula II, which are prepared through the following steps;

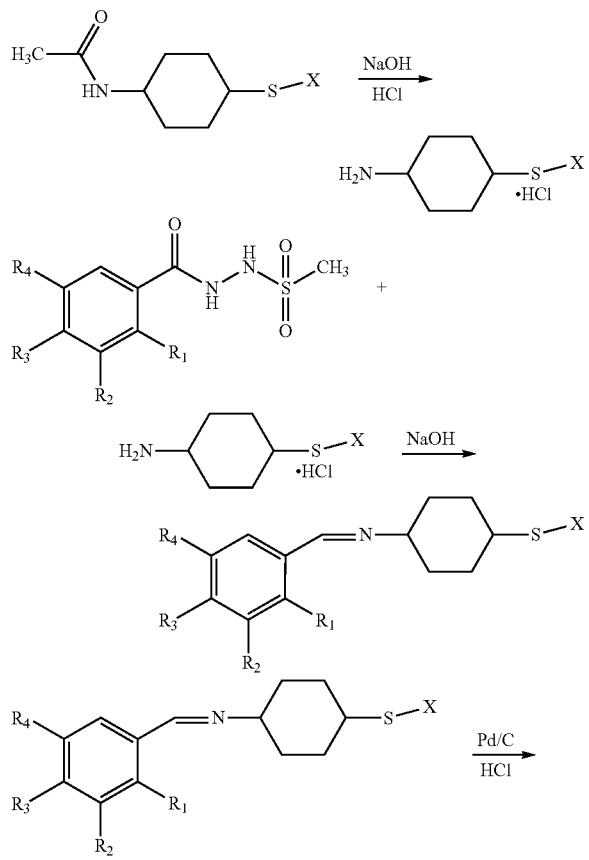

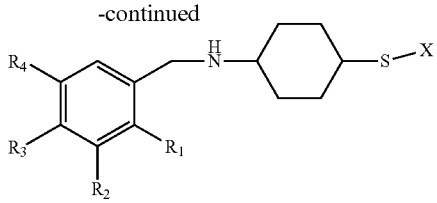

The second aspect of the present disclosure relates to a pharmaceutical composition comprising at least one compound represented by formula I and formula II, or a pharmaceutically acceptable salt thereof, and one or more pharmaceutically acceptable carriers or excipients.

The third aspect of the present disclosure relates to compounds of formula I and formula II and non-toxic pharmaceutically acceptable salts thereof, and to the use of compounds of formula I and formula II and non-toxic pharmaceutically acceptable salts thereof as active ingredient in the pharmaceutical composition as an expectorant.

The compounds represented by formula I and formula II can form pharmaceutically acceptable salts with inorganic acids such as hydrochloride, hydrobromide, sulfate and the like. Selection and preparation of appropriate salts are well known to those skilled in the art.

The compounds of the present disclosure, or pharmaceutically acceptable salts thereof, may be administered alone or in a form of pharmaceutical compositions. The pharmaceutical compositions of the present disclosure can be formulated into various suitable dosage forms based on the administration route. One or more physiologically acceptable carriers including excipients and auxiliaries are employed, which facilitate processing of the active compounds into preparations which can be used pharmaceutically. Appropriate forms of formulation depend on the route of administration chosen and can be prepared according to general knowledge well known in the art.

The route of administration can be oral, parenteral or topical, preferably oral, aerosol inhalation and injection. Pharmaceutical preparations that can be administered orally include oral liquids, granules or tablets and the like. Those skilled in the art will understand that the compounds of the present disclosure can be used with a suitable drug delivery system (DDS) to produce more favorable effects.

DETAILED DESCRIPTION OF THE EMBODIMENTS

The following examples facilitates comprehensive understanding of the present disclosure, however, they do not limit to the present disclosure in any way.

Example 1

Preparation of trans-4-aminocyclohexanethiol hydrochloride

To a 500 ml reaction flask were added 40 g of trans-4-acetamidocyclohexanethiol, 40 g of potassium hydroxide and 350 ml of water, and the reaction flask was placed in an oil bath, and heated under reflux for 10 hours. Upon termination of the reaction, the reaction mixture was extracted with dichloromethane (100 ml×3); the organic phases were combined, dried over anhydrous sodium carbonate, filtered. Hydrogen chloride was introduced into the filtrate, and when no solid were further produced, the filtrate was cooled down to 0° C. and was stirred and crystallized for 10 hours, and filtered to give 38 g of trans-4-aminocyclohexanethiol hydrochloride.

Example 2

Preparation of trans-4-[(2-amino-3,5-dibromo-benzylidene)amino]-cyclohexanethiol To a 1000-ml three-necked bottle were added trans-4-aminocyclohexanethiol hydrochloride (50 g), sodium hydroxide (13 g), potassium carbonate (18 g), and ethylene glycol monomethyl ether (400 ml), and the bottle was place in an oil bath, and heated to 120° C. N-(2-amino-3,5-dibromo-benzoyl)-N-methanesulfonyl hydrazide (78 g) was added in 4 batched. Upon completion of addition, the resulting mixture was heated under reflux for 2 h, and then the reaction system was cooled to room temperature. Water (400 ml) was added and stirred for crystallization. The crystals were filter to afford 132 g of trans-4-[(2-amino-3,5-dibromo-benzylidene)amino]-cyclohexanethiol.

Example 3

Preparation of trans-4-[(2-amino-3,5-dibromo-benzyl)amino]-cyclohexanethiol hydrochloride (I1)

To a hydrogenation reactor were added trans-4-[(2-amino-3,5-dibromo-benz ylid-ene)amino]-cyclohexanethiol (100 g), and glacial acetic acid 300 ml, 5 wt % pd/C 1.0 g. And hydrogenation was carried out for 8 h at 0.2 MPa, 60° C. Upon completion of the reaction, the solvents were removed under reduced pressure, and the resulting residue was dissolved in 400 ml of acetone, then 10 ml of hydrochloric acid was added dropwise. The temperature was lowered to 0° C. and crystallized for 4 h, the crystals were filtered and dried to afford trans-4-[(2-amino-3,5-dibromo-benzyl)amino]-cyclo hexanethiol hydrochloride (I1).

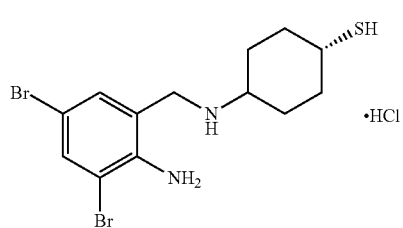

I1

Examples 4-5

The operations were referred to Examples 1, 2, and 3, except that trans-4-aminocyclohexanethiol hydrochloride is replaced with 3-amino cyclohexanethiol hydrochloride to give the following compound of formula I.

| Example | 3-aminocyclohexanethiol hydrochloride | product |
|---|---|---|
| 4 | trans-3-aminocyclohexanethiol hydrochloride | I2 |
| 5 | cis-3-aminocyclohexanethiol hydrochloride | I3 |

Example 6

Preparation of trans-4-[(2-amino-3,5-dibromo-benzyl)-methyl-amino]-cyclohexanethiol hydrochloride (I4)

The operations were referred to Examples 1, 2, and 3, except that trans-4-aminocyclohexanethiol hydrochloride is replaced with 4-methylamino-cyclohexanethiol hydrochloride to afford compound I6.

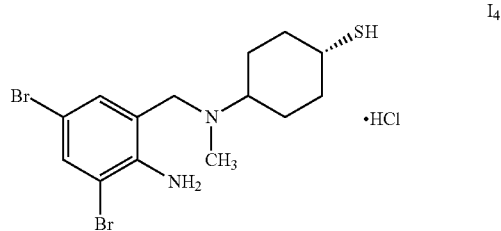

I4

Examples 7-10

The operations were referred to Example 6, except that 4-methylamino-cyclohexanethiol hydrochloride was replaced with methylamino-cyclohexanethiols having different –SH group positions and isomers to give the compound of formula I below.

| Example | 4-methylamino-cyclohexanethiol | product |
|---|---|---|
| 7 | trans-3-methylamino-cyclohexanethiol | I5 |
| 8 | cis-3-methylamino-cyclohexanethiol | I6 |
| 9 | trans-2-methylamino-cyclohexanethiol | I7 |
| 10 | cis-2-methylamino-cyclohexanethiol | I8 |

Example 11

Preparation of cis-3-(4-amino-2-chloro-benzylamino)-cyclohexanethiol (I9)

Ten grams of cis-3-(2-chloro-4-nitro-benzylamino)-cyclohexanethiol hydrochloride was dissolved in 150 ml of ethanol and 20 ml of water, the resulting solution was mixed with 0.2 g of palladium carbon, and hydrogenation was carried out at room temperature to reduce the resulting mixture. After the hydrogen absorption is completed, the palladium carbon was removed by filtration, and a small amount of ether was added to the filtrate to precipitate a solid, and the solids were collected and recrystallized from ethanol to give the compound (I9).

Example 12

Preparation of cis-3-(2-amino-5-bromo-benzylamino)-cyclohexanethiol (I10)

Thirty grams of lithium aluminum hydride was added to 3 L of anhydrous tetrahydrofuran, and the mixture was added dropwise to a solution of 100 g of cis-2-amino-4-chloro-N-(3-mercapto-cyclohexyl)-benzamide in anhydrous tetrahydrofuran. After all the mixture was dripped, the resulting mixture was and refluxed with stirring for 24 hours.

Then ethyl acetate and 5N sodium hydroxide were added to quench the unreacted lithium aluminum hydride. Filtration was conducted and the filtrate was concentrated to dryness under vacuum. The residue was purified by silica gel column chromatography to give compound (I10).

Examples 13-14

The operations were referred to Example 12, the difference was that different benzamide compounds were reduced to afford the following compounds of formula I.

| Example | benzamide | product |
|---------|-----------|---------|
| 13 | cis-2-amino-4-chloro-N-(3-mercapto-cyclohexyl)-benzamide | I11 |
| 14 | trans-2-amino-6-chloro-N-(4-mercapto-cyclohexyl)-benzamide | I12 |

Example 15

Preparation of trans 3-[4-(2-amino-3,5-dibromo-benzylamino)-cyclohexylsulfanyl]-propan-1-ol (I13)

Compound I1 (24.55 g, 0.057 mol) was added into 100 ml of water, stirred to dissolve all the solids, and 12. 40 g (0.172 mol) allyl alcohol, 1 g (0.0037 mol) $K_2S_2O_8$, and 0.38 g (0.0037 mol) $NaHSO_3$ were added in sequence under stirring. The resulting mixture was heated to 50° C., stirred for 8 hours. After the reaction was completed, water and excess allyl alcohol were distilled off, 200 ml of absolute ethanol was added, stirred to precipitate a solid, and the solids were purified to give Compound I13.

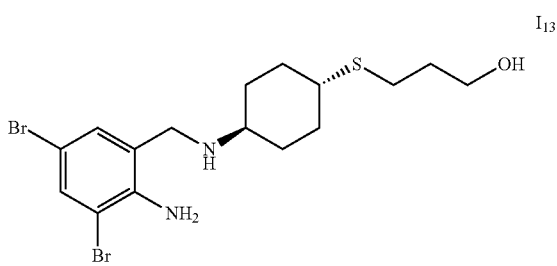 [SMILES: Nc1c(Br)cc(Br)cc1CN[C@H]1CC[C@H](SCCCO)CC1]

I13

Example 16

In Vivo Pharmacodynamic Test—Expectorant Test in Mice Using a Phenol Red Method

In this example, the in vivo efficacy of the compounds I1, I4, I13 of the present disclosure and known compounds was tested.

Ninety healthy mice were randomly divided into 9 groups, and the specific grouping is shown in Table 2. Mice in the positive control group were give medicinal ammonium chloride and ambroxol hydrochloride orally, mice in the normal control group were given normal saline of the same amount, and mice the other groups were given corresponding drugs by gavage. The mice were administered by gavage once in the morning and afternoon (excluding ammonium chloride) 2 days before the experiment. After 1 hour of intragastric administration on the morning of the experiment, the mice were intraperitoneally injected with 0.5 ml of phenol red, and the mice were sacrificed 0.5 hours later. The tissue surrounding the organs was peeled off, and a section of the trachea from the thyroid cartilage to the branch of the trachea was cut off and placed in a test tube containing 2 ml of normal saline. The tube was shaken for 30 minutes, the trachea was discarded, and 0.2 ml of sodium hydroxide (1 mol/L) was added to each sample solution. The OD value was measured using a UV-visible spectrophotometer at a wavelength of 546 nm, and the absorbance values were converted into the phenol red content according to the phenol red standard curve.

| Group | n | Dose/(ml/kg) | Tracheal phenol red excretion/(mg/L) |
|-------|---|--------------|--------------------------------------|
| Normal group | 10 | / | 0.250 ± 0.305 |
| Ammonium chloride group | 10 | 1.0 | 0.875 ± 0.208 ΔΔ** |
| Ambroxol group | 10 | 2.0 | 1.418 ± 0.352 ΔΔ** |
| Acetylcysteine | 10 | 2.0 | 1.532 ± 0.247 ΔΔ** |
| I1 high dose group | 10 | 2.0 | 1.610 ± 0.284 ΔΔ** |
| I1 low dose group | 10 | 0.5 | 1.225 ± 0.337 ΔΔ** |
| I4 high dose group | 10 | 2.0 | 1.273 ± 0.275 ΔΔ** |
| I4 low dose group | 10 | 0.5 | 1.083 ± 0.312 ΔΔ** |
| I13 high dose group | 10 | 2.0 | 1.826 ± 0.334 ΔΔ** |
| I13 low-dose group | 10 | 0.5 | 1.452 ± 0.351 ΔΔ** |

Note:
ΔΔ $P < 0.01$ when compared with normal group; * $P < 0.05$ when compared with ambroxol oral solution group; ** $P < 0.01$; ✕ $P < 0.05$; ✕✕ $P < 0.05$ when compared with the ammonium chloride group.

The data was processed by PEMS medical statistical software. The results showed that each medication group significantly promoted the secretion of phenol red in the tracheal segment of mice. The ambroxol group and the high dose of compounds I1 and I13 had the best effect, and the compound I13 had the strongest effect. The effect produced by each dose was significantly better than that of ammonium chloride and ambroxol, among which compound I13 had the most significant expectorant effect. It is suggested that the expectorant effect of compound I13 is enhanced with the increase of dose, and there is a relatively obvious dose-effect relationship, and compound I13 has better the effect than compound I1.

Example 17

Acute toxicity test of the compound of the present disclosure to mice administered intravenously To test the acute toxicity of compounds of the present disclosure and comparative compounds, the following experiments were performed.

Compounds of the present disclosure were dissolved in water and administered to 5 ICR mice (mice of 5-week old, male, weighing 20 g±2 g). Intravenous administration was performed to determine the median lethal dose (LD50, mg/kg). Ambroxol hydrochloride was used as a control. The results are shown in the table below.

| compound | median lethal dose (LD50, mg/kg) |
|----------|----------------------------------|
| Ambroxol hydrochloride | 268 |
| I1 compound | 453 |
| I4 compound | 523 |
| I13 compound | 507 |

The test results show that the LD50 values for compounds I1, I4 and I13 are much higher than that for ambroxol hydrochloride, suggesting that the safety of the compounds of the present disclosure is better than that of ambroxol hydrochloride.

Formula used in the Examples: preparation of pharmaceutical composition

1. Preparation of Powder

| Compound Example 3 | 2 g |
|---|---|
| Lactose | 1 g |

The above materials were mixed, and the mixture was filled into a sealed package to prepare a powder.

2. Preparation of Tablets

| Compound of Example 4 | 500 g |
|---|---|
| Corn starch | 100 g |
| Lactose | 100 g |
| Magnesium Stearate | 2 g |

The above materials were mixed and the mixture was then compressed into tablets by known methods.

3. Preparation of Capsules

| Compound of Example 11 | 500 g |
|---|---|
| Corn starch | 100 g |
| Lactose | 100 g |
| Magnesium Stearate | 2 g |

Capsules were prepared by mixing the above materials and filling the mixture into gelatin capsules by known methods.

4. Preparation of Injections

| Compound of Example 13 | 20 g |
|---|---|
| pH adjuster to maintain pH between | 4.0-9.0 |
| Glucose | excipient |
| Water | solvent |

The compound of Example 13 and glucose were dissolved in water, the pH was adjusted to 4.0-9.0 with a pH adjuster, and the solution was freeze-dried in a freeze-drying oven. After drying, the vials were plugged and capped.

5. Preparation of Inhalants

| Compound of Example 13 | 15 g |
|---|---|
| pH adjuster to maintain pH between | 4.0-9.0 |
| Sodium chloride 15 g | isoosmotic adjusting agent |
| Water | 2000 ml |

The compound of Example 13 and sodium chloride were dissolved in water, the pH was adjusted to 4.0-9.0 with a pH adjuster (hydrochloric acid or sodium hydroxide), the solution was filled in vials and capped, and the vials were sterilized at 121° C. for 12 minutes in an autoclave to obtain the inhalants.

What is claimed is:

1. A compound represented by formula I, or a pharmaceutically acceptable salt or tautomer thereof;

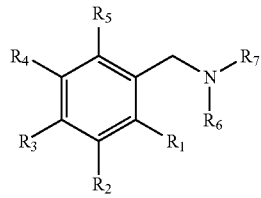

I wherein $R_1$ represents H, F, Cl, Br or $NH_2$; $R_2$ represents H, F, Cl or Br; $R_3$ represents H, F, Cl, Br or $NH_2$; $R_4$ represents H, F, Cl or Br; $R_5$ represents H, F, Cl or Br; $R_6$ represents H or $CH_3$; and $R_7$ represents

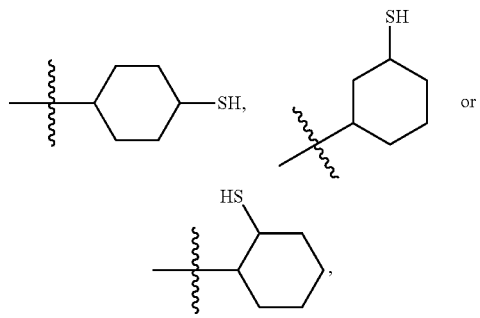

and wherein not all of $R_1$, $R_2$, $R_3$, $R_4$, and $R_5$ are hydrogen.

2. A compound represented by formula II, pharmaceutically acceptable salt or tautomer thereof;

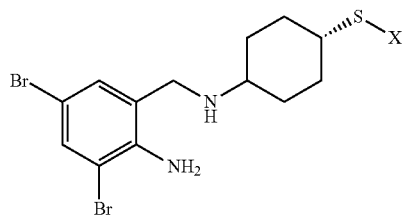

II wherein X represents

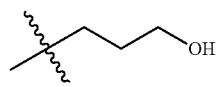 [SMILES: *CCCO]

or amino acid salts thereof.

3. The compound, pharmaceutically acceptable salt or tautomer thereof according to claim 1, wherein the compound is selected from the group consisting of:
- I1: trans-4-[(2-amino-3,5-dibromo-benzyl)amino]-cyclohexanethiol
- I2: trans-3-[(2-amino-3,5-dibromo-benzyl)amino]-cyclohexanethiol
- I3: cis-3-[(2-amino-3,5-dibromo-benzyl)amino]-cyclohexanethiol I4: trans-4-[(2-amino-3,5-dibromo-benzyl)-methylamino]-cyclohexanethiol I5: trans-4-[(2-amino-3,5-dibromo-benzyl)-methylamino]-cyclohexanethiol I6: cis-3-[(2-amino-3,5-dibromo-benzyl)-methylamino]-cyclohexanethiol I7: trans-2-[(2-amino-3,5-dibromo-benzyl)-methylamino]-cyclohexanethiol I8: cis-4-[(2-amino-3,5-dibromo-benzyl)-methylamino]-cyclohexanethiol I9: cis-3-[(4-amino-2-chloro-benzyl)amino]-cyclohexanethiol I10: cis-3-[(2-amino-5-bromo-benzyl)amino]-cyclohexanethiol I11: cis-3-[(2-amino-4-chloro-benzyl)amino]-cyclohexanethiol I12: trans-4-[(2-amino-6-chloro-benzyl)-methylamino]-cyclohexanethiol I13: trans-3-[4-(2-amino-3,5-dibromo-benzylamino)-cyclohexylsulfanyl]-propane-1-ol.

4. The compound, pharmaceutically acceptable salt or tautomer thereof, according to claim 1, wherein the compound represented by formula I is an organic base which is capable of forming a water-soluble salt reacting with one or two molar equivalents of an inorganic or organic acid.

5. The compound, pharmaceutically acceptable salt thereof, or a tautomer thereof, according to claim 1, wherein the pharmaceutically acceptable salt comprises one of a hydrochloride salt, a hydrobromide salt, or a sulfate salt.

6. The compound, pharmaceutically acceptable salt or tautomer thereof according to claim 1 further comprising one or more pharmaceutically acceptable carriers or excipients.

7. A method for eliminating phlegm in a patient, comprising a step of administering the compound, or the pharmaceutically acceptable salt thereof or the tautomer thereof, according to claim 1 to a patient in need thereof.

8. The compound, pharmaceutically acceptable salt or tautomer thereof according to claim 2, where the compound is selected from the group consisting of:

I1: trans-4-[(2-amino-3,5-dibromo-benzyl)amino]-cyclohexanethiol

I2: trans-3-[(2-amino-3,5-dibromo-benzyl)amino]-cyclohexanethiol

I3: cis-3-[(2-amino-3,5-dibromo-benzyl)amino]-cyclohexanethiol

I4: trans-4-[(2-amino-3,5-dibromo-benzyl)-methylamino]-cyclohexanethiol

I5: trans-4-[(2-amino-3,5-dibromo-benzyl)-methylamino]-cyclohexanethiol

I6: cis-3-[(2-amino-3,5-dibromo-benzyl)-methylamino]-cyclohexanethiol

I7: trans-2-[(2-amino-3,5-dibromo-benzyl)-methylamino]-cyclohexanethiol

I8: cis-4-[(2-amino-3,5-dibromo-benzyl)-methylamino]-cyclohexanethiol

I9: cis-3-[(4-amino-2-chloro-benzyl)amino]-cyclohexanethiol

I10: cis-3-[(2-amino-5-bromo-benzyl)amino]-cyclohexanethiol

I11: cis-3-[(2-amino-4-chloro-benzyl)amino]-cyclohexanethiol

I12: trans-4-[(2-amino-6-chloro-benzyl)-methylamino]-cyclohexanethiol

I13: trans-3-[4-(2-amino-3,5-dibromo-benzylamino)-cyclohexylsulfanyl]-propane-1-ol.

9. The compound, pharmaceutically acceptable salt or tautomer thereof according to claim 2, wherein the compound represented by formula II is an organic base which is capable of forming a water-soluble salt reacting with one or two molar equivalents of an inorganic or organic acid.

10. The compound, pharmaceutically acceptable salt or tautomer thereof according to claim 2, wherein the pharmaceutically acceptable salt is one of a hydrochloride salt, a hydrobromide salt, or a sulfate salt.

11. The compound, pharmaceutically acceptable salt or tautomer thereof according to claim 3, wherein the pharmaceutically acceptable salt is one of a hydrochloride salt, a hydrobromide salt, or a sulfate salt.

12. The compound, pharmaceutically acceptable salt or tautomer thereof according to claim 2, further comprising one or more pharmaceutically acceptable carriers or excipients.

13. The compound, pharmaceutically acceptable salt or tautomer thereof according to claim 3, further comprising, one or more pharmaceutically acceptable carriers or excipients.

14. The compound, pharmaceutically acceptable salt or tautomer thereof according to claim 4, further comprising one or more pharmaceutically acceptable carriers or excipients.

15. A method for eliminating phlegm in a patient, comprising a step of administering the compound, or the pharmaceutically acceptable salt or tautomer thereof according to claim 2 to a patient in need thereof.

16. A method for eliminating phlegm in a patient, comprising a step of administering the compound, or the pharmaceutically acceptable salt or tautomer thereof according to claim 3 to a patient in need thereof.

17. A method for eliminating phlegm in a patient, comprising a step of administering the compound, or the pharmaceutically acceptable salt or tautomer thereof according to claim 4 to a patient in need thereof.

18. A method for eliminating phlegm in a patient, comprising a step of administering the compound, or the pharmaceutically acceptable salt or tautomer thereof according to claim 5 to a patient in need thereof.

* * * * *